US00PP15731P2

(12) United States Plant Patent
Amorao et al.

(10) Patent No.: US PP15,731 P2
(45) Date of Patent: Apr. 26, 2005

(54) STRAWBERRY PLANT NAMED 'DRISCOLL AGOURA'

(50) Latin Name: *Fragaria×ananassa*
Varietal Denomination: Driscoll Agoura

(75) Inventors: Amado Q. Amorao, Camarillo, CA (US); Arnoldo Solis, Jr., Oxnard, CA (US); Michael Ferguson, Chatsworth, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 41 days.

(21) Appl. No.: 10/271,417

(22) Filed: Oct. 15, 2002

(51) Int. Cl.[7] ..... A07H 5/00
(52) U.S. Cl. ..... Plt./209
(58) Field of Search ..... Plt./209

*Primary Examiner*—Bruce R. Campell
*Assistant Examiner*—Michelle Kizilkaya
(74) *Attorney, Agent, or Firm*—Jones Day

(57) ABSTRACT

This invention relates to a new and distinct variety of strawberry named 'Driscoll Agoura'. The variety is similar to the varieties 'El Capitan' and 'San Miguel'. The variety is distinguished from 'El Capitan' and 'San Miguel', in particular, by its weak vigor, obtuse to slightly oblique terminal leaflet base, few stolons, dense stolon pubescence, flat fruiting truss at first picking, strong unevenness of fruit surface, and medium sweetness of the fruit.

5 Drawing Sheets

Latin name of the genus and species of the plant claimed: The variety is botanically identified as *Fragaria×ananassa*.

1. BACKGROUND OF THE INVENTION

The new variety originated as a result of a controlled cross between the strawberry plants '61C117' (unpatented Driscoll variety) and '19A268' (unpatented Driscoll variety) in an ongoing breeding program, and was discovered as a seedling in a controlled breeding plot in, Ventura County, Calif. in February, 1998. The original seedling of the new cultivar was asexually propagated by stolons at a nursery in Shasta County, Calif. Propagules were transplanted to a controlled breeding plot in Ventura County, Calif., where it was identified and selected for further evaluation. 'Driscoll Agoura' was subsequently asexually propagated and underwent further testing at various locations in Ventura County, Calif. for four years. This propagation and testing has demonstrated that the combination of traits disclosed herein which characterize the new variety are fixed and retained true to type through successive generations of asexual reproduction.

2. SUMMARY OF THE INVENTION

The present invention relates to a new and distinct variety of strawberry named 'Driscoll Agoura'. The variety is botanically identified as *Fragaria×ananassa*. The new variety is distinguished from other varieties by a number of characteristics as set forth in Tables 1–6.

3. COMPARISON TO SIMILAR VARIETIES

The varieties which we believe to be similar to 'Driscoll Agoura' from those known to us are 'El Capitan' (U.S. Plant Pat. No. P.P. 14,005 P3), and 'San Miguel' (U.S. Plant Pat. No. P.P. 10,642, issued Oct. 13, 1998). There are several characteristics of the new variety that are different from, or not possessed by 'El Capitan', and 'San Miguel'. The new variety has a weak vigor, obtuse to slightly oblique terminal leaflet base, few stolons, dense stolon pubescence, flat fruiting truss at first picking, strong unevenness of fruit surface, and medium sweetness of the fruit.

'Driscoll Agoura' differs from its parent '61C117' (unpatented Driscoll variety) in several characteristics, including, but not limited to, having greater berry size and greater early season production. 'Driscoll Agoura' differs from its parent '19A268' (unpatented Driscoll variety) in several characteristics, including, but not limited to, having less creaing on the primary berries.

4. BRIEF DESCRIPTION OF THE DRAWINGS

The accompanying photographs show typical specimens of the new variety, including fruit, foliage and flowers, in color as nearly true as it is reasonably possible to make in color illustrations of these characteristics. The plants of 'Driscoll Agoura' characterized in the botanical descriptions and depicted in the figures were grown outdoors in an annular production system. Measurements were taken during the spring in the second half of the production season, approximately seven months after planting.

5. DESCRIPTION OF THE NEW VARIETY

Figure 1:
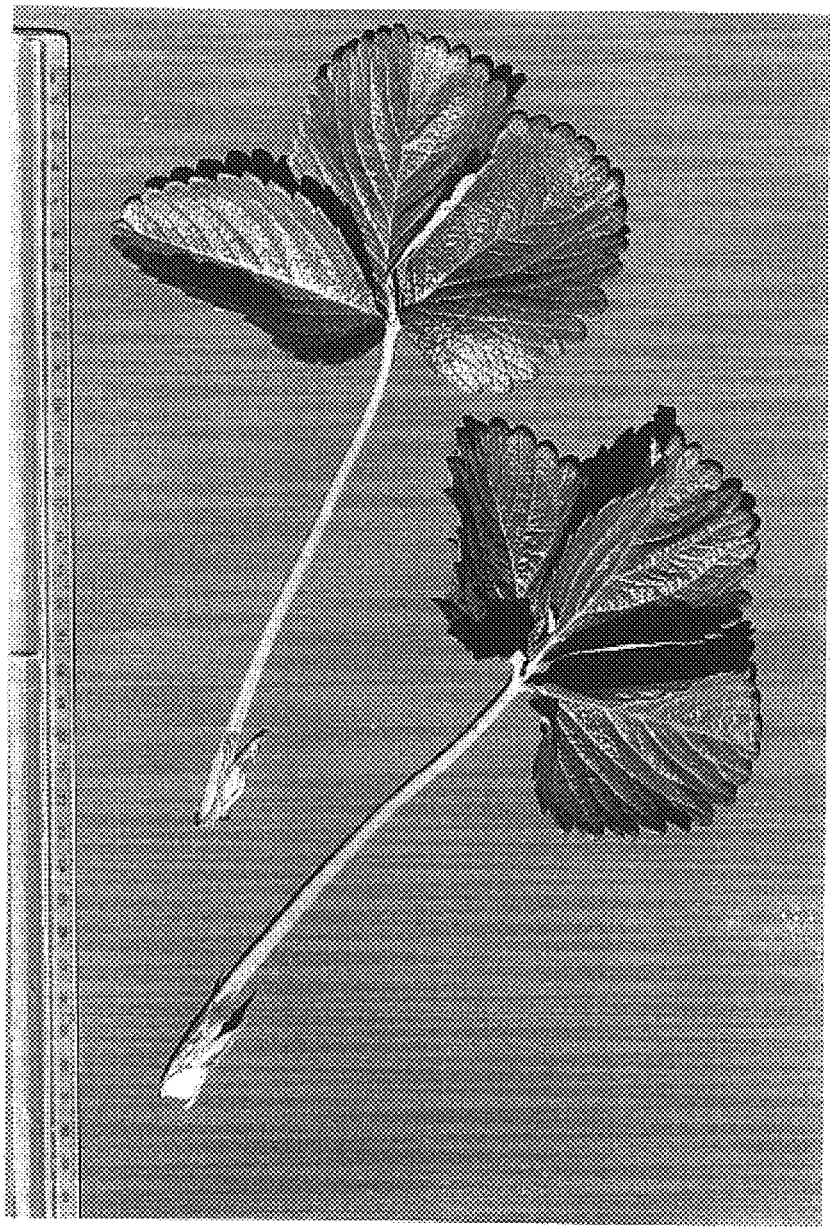
FIG. 1 shows leaves of the plant with three leaflets.
Figure 2:
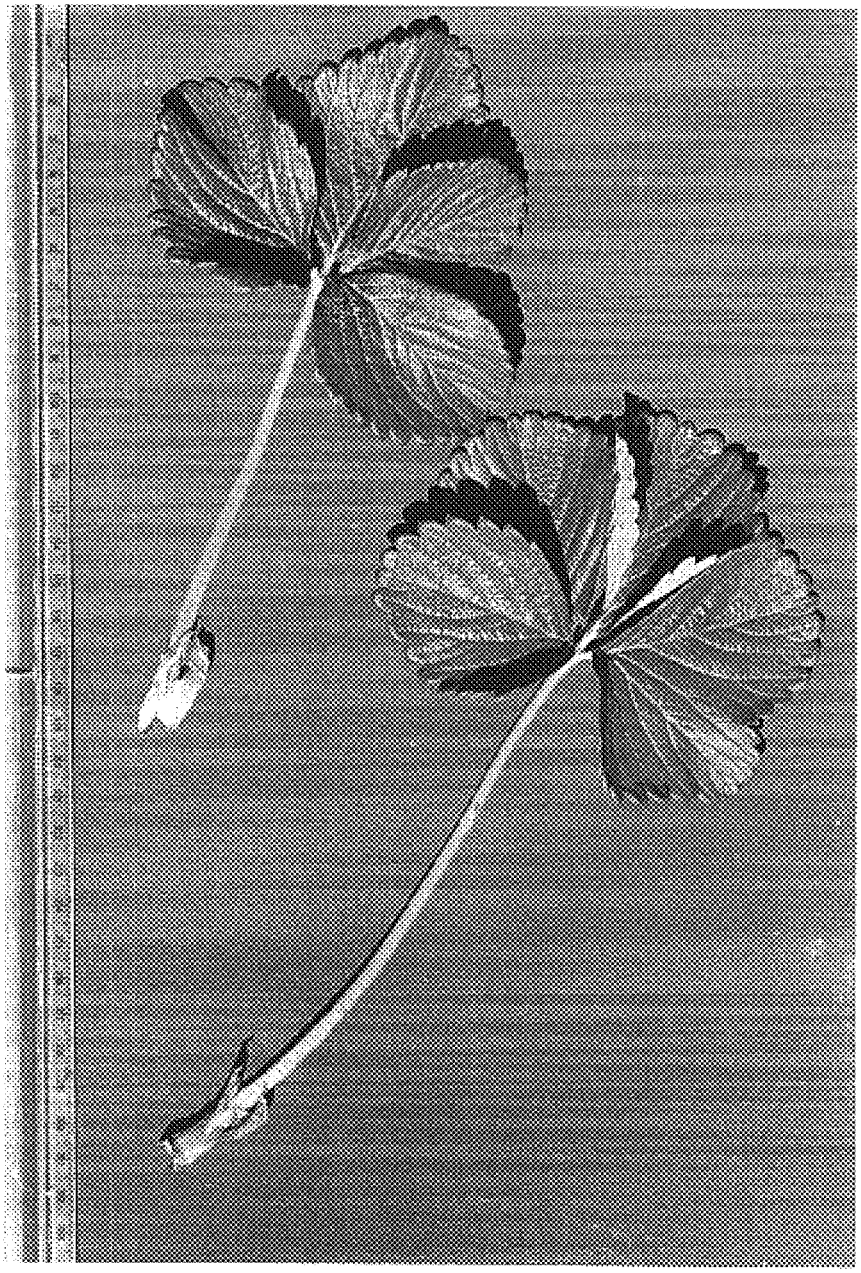
FIG. 2 shows leaves of the plant with four leaflets.
Figure 3:
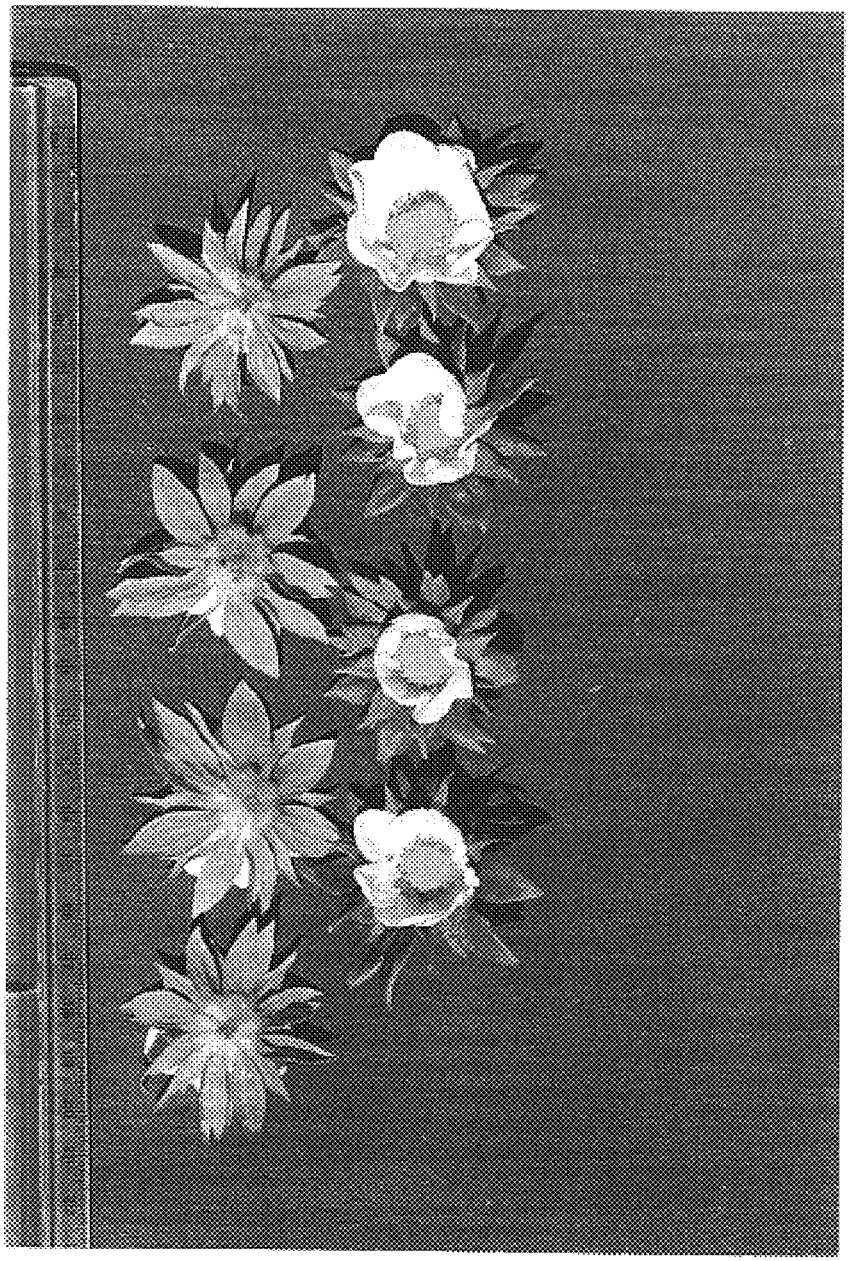
FIG. 3 shows the upper side and under side of the flowers.
Figure 4:
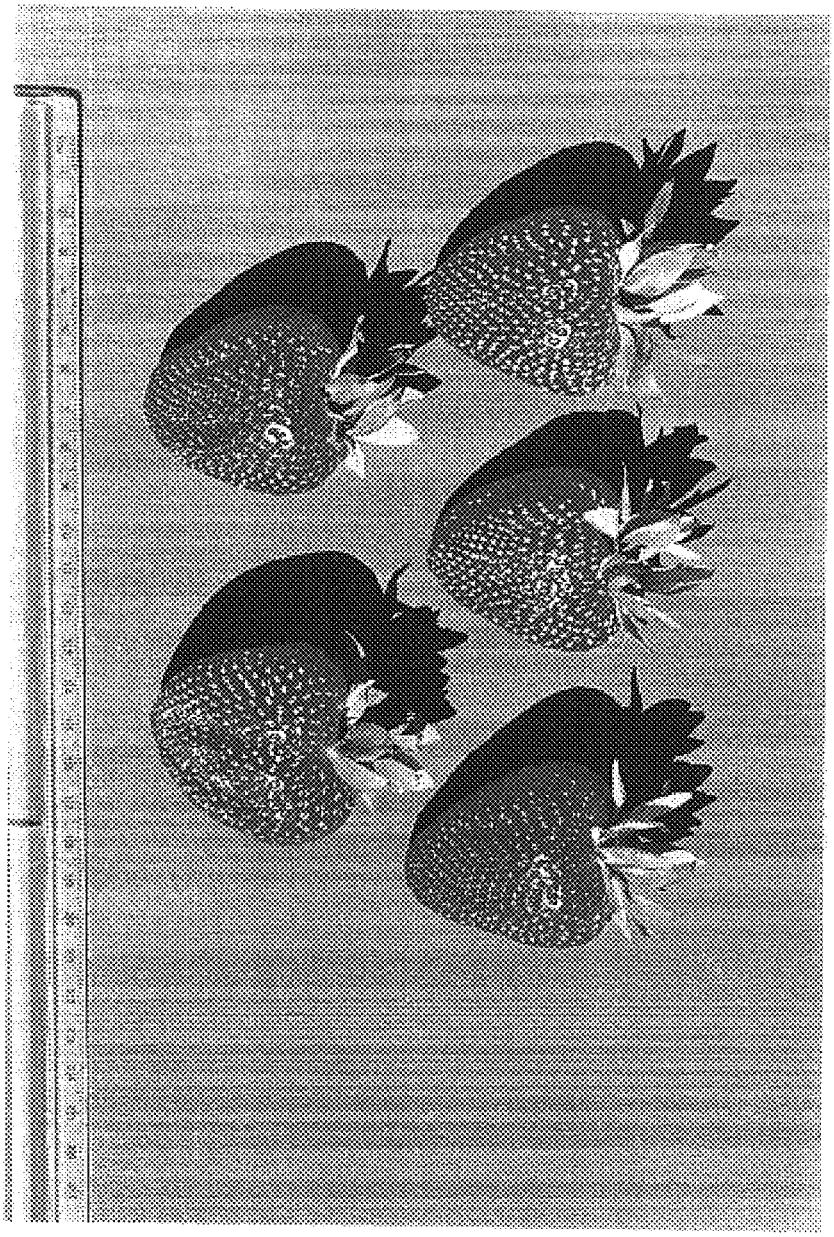
FIG. 4 shows a close-up of the strawberry.
Figure 5:
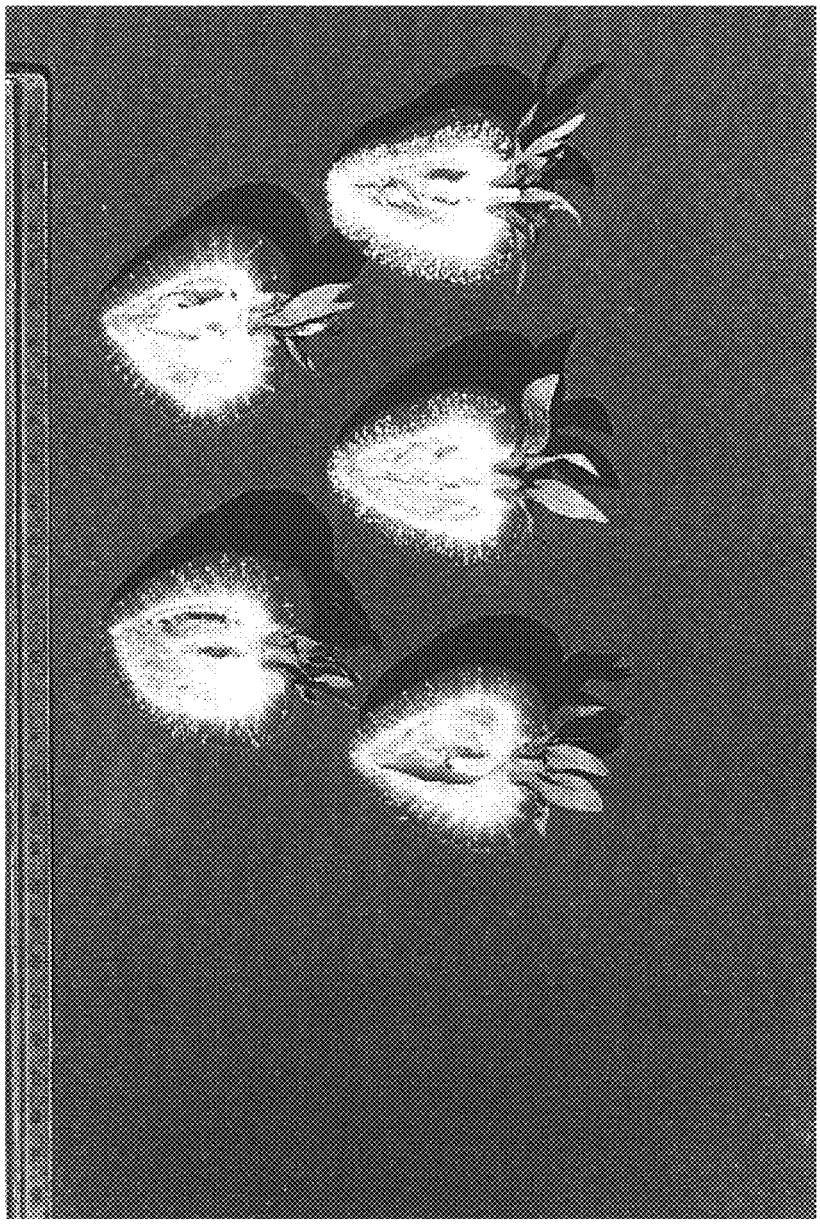
FIG. 5 shows the strawberry in longitudinal cross-section.

The following detailed description of the new variety is based upon observations taken of plants and fruit grown in Ventura County, Calif., U.S.A. Observations of 'Driscoll Agoura', 'El Capitan' and 'San Miguel' were taken in side by side comparison in 2002. This description is in accordance with UPOV terminology. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

5.1 PROPAGATION

The new variety is principally propagated by way of stolons. Although propagation by stolons is presently preferred, other known methods of propagating strawberry plants may be employed.

5.2 CHARACTERISTICS OF THE NEW VARIETY

Information on the new variety is presented in Tables 1, 2 and 3. In the tables, the flowers described are secondary flowers except where indicated. The fruit described is the secondary fruit on one year old plants. Fruit and flower measurements are an average of both primary and secondary fruit and flowers. In particular, the reproductive structures of 'Driscoll Agoura' are fully self-fertile and typical of the species. Anther color is yellow, 14A and receptacle color is 9A yellow.

Table 1 provides information on the plant and fruit characteristics of the new variety 'Driscoll Agoura' compared with characteristics of 'El Capitan' and 'San Miguel'. Table 2 provides additional information of the plant and fruit characteristics of the new variety 'Driscoll Agoura' compared with characteristics of the varieties 'El Capitan' and 'San Miguel'. Table 3 provides reactions of the new variety to stresses as compared to the varieties 'El Capitan' and 'San Miguel'. Tables 4 and 5 provide information of the new variety's reaction to pests and diseases, respectively, compared to the varieties 'El Capitan' and 'San Miguel'. Table 6 provides isozyme characteristics of the new variety as compared to the varieties 'El Capitan' and 'San Miguel'.

TABLE 1

DETAILED COMPARISON OF 'DRISCOLL AGOURA', 'EL CAPITAN' AND 'SAN MIGUEL'

| | Driscoll Agoura | El Capitan | San Miguel |
|---|---|---|---|
| Plant Characteristics | | | |
| Height of Plant (cm) | 19.1 | 25.9 | 23.3 |
| Spread of Plant (cm) | 30.1 | 35.2 | 32.5 |
| Number of Crowns | 2.8 | 4.0 | 3.3 |
| Leaf Characteristics | | | |
| Terminal Leaflet Width (cm) | 6.6 | 6.7 | 6.2 |
| Terminal Leaflet Length (cm) | 6.0 | 5.7 | 6.6 |
| Terminal Leaflet Length/Width Ratio | 1.10 | 1.17 | 0.94 |
| Number of Teeth/Terminal Leaflet | 22.0 | 17.1 | 23.3 |
| Color of upper side of leaf | dark green 147A | dark green 147A | medium to dark green 147A |
| Color of under side of leaf | light to medium green 138B | light to medium green 147C | light to medium green 138B |
| Petiole Length (cm) | 15.5 | 19.0 | 17.1 |
| Petiole color | 149A | 149A | 149A |
| Bract Frequency | 25% typically single | 8% typically single | 8% typically paired |
| Stipule Length (cm) | 3.3 | 3.8 | 3.3 |
| Stipule Width (cm) | 1.1 | 1.1 | 1.1 |
| Flower Characteristics | | | |
| Petal Width (cm) | 1.27 | 1.43 | 1.37 |
| Petal Length (cm) | 1.15 | 1.48 | 1.35 |

TABLE 1-continued

DETAILED COMPARISON OF 'DRISCOLL AGOURA', 'EL CAPITAN' AND 'SAN MIGUEL'

| | Driscoll Agoura | El Capitan | San Miguel |
|---|---|---|---|
| Petal Length/Width Ratio | 1.10 | 0.97 | 1.01 |
| Petal Color | 155C | 155C | |
| Flower Diameter (cm) | 2.26 | 2.75 | 2.65 |
| Calyx Diameter (cm) | 3.44 | 3.75 | 2.90 |
| Fruit Characteristics | | | |
| Fruit Width (cm) | 4.09 | 4.59 | 4.67 |
| Fruit Length (cm) | 3.97 | 4.01 | 4.18 |
| Fruit Length/Width Ratio | 1.03 | 1.14 | 1.12 |
| Average Berry Size (g) | 25.7 | 23.0 | 24.0 |
| Fruit Skin Color | dark red 53A | dark red 53A | dark red 53A |
| Fruit Flesh Color | orange red 41A | red 43A | dark red 45A |
| Average % brix | 7.92 | 7.68 | 7.24 |
| Brix/Acid Ratio | 10.12 | 9.70 | 9.51 |
| Achene Coloration | dark red to yellow 59A to 151A | dark red to yellow green 60A to 151A | dark red to yellow green 53A to 151B |
| Total Yield (g/plant) | 621 | 665 | 650 |

TABLE 2

CHARACTERISTICS OF 'DRISCOLL AGOURA', 'EL CAPITAN' AND 'SAN MIGUEL'

| | Driscoll Agoura | El Capitan | San Miguel |
|---|---|---|---|
| Plant | | | |
| Habit | flat globose | globose | flat globose |
| Density | open | medium dense | open |
| Vigor | weak | medium | medium |
| Leaf | | | |
| Shape in cross section | slightly concave to flat | slightly concave | concave |
| Interveinal blistering | strong | strong | strong |
| Glossiness | medium | strong | strong |
| Number of leaflets | more than 3 leaflets on approx. 17% of leaves | three only | three only |
| Terminal leaflet margin profile | flat | flat | flat to revolute |
| Terminal leaflet shape of base | obtuse to slightly oblique | rounded | rounded |
| Terminal leaflet shape of teeth | rounded | obtuse | rounded |
| Stipule pubescence | sparse | sparse to medium | sparse |
| Petiole pubescence | dense | dense | sparse to medium |
| Petiole pose of hairs | outwards | outward to downward | outward |
| Stolon | | | |
| Number | few | many | many |
| Anthocyanin coloration | weak to medium | medium to strong | weak to medium |
| Thickness | medium thick | thin | thin to medium |
| Pubescence | dense | sparse to medium | sparse to medium |
| Inflorescence | | | |
| Position relative to foliage | above | above | above |

TABLE 2-continued

CHARACTERISTICS OF 'DRISCOLL AGOURA', 'EL CAPITAN' AND 'SAN MIGUEL'

| | Driscoll Agoura | El Capitan | San Miguel |
|---|---|---|---|
| Diameter of calyx relative to corolla | larger | larger | larger |
| Diameter of inner calyx relative to outer | same size | smaller to same size | same size |
| Spacing of petals | overlapping | overlapping | overlapping |
| Fruiting Truss | | | |
| Attitude at first picking | Flat | prostrate | prostrate |
| Average Length (cm) | 12.3 | 18.4 | 17.4 |
| Fruit | | | |
| Predominant shape | wedged to cordate | cordate | conical to cylindrical |
| Difference in shapes between primary and secondary fruits | marked, primaries are more creased | marked | moderate |
| Bands without achenes | very narrow | very narrow | very narrow |
| Unevenness of surface | strong | weak to medium | weak to medium |
| Evenness of color | slightly uneven | slightly uneven to even | even |
| Glossiness | strong | strong | medium |
| Insertion of achenes | level with surface | below to level with the surface | below surface |
| Insertion of calyx | set above fruit | in a basin to level | set above |
| Pose of the calyx segments | reflexed | reflexed | spreading to reflexed |
| Size of calyx in relation to fruit | smaller to same size | larger | same size |
| Adherence of calyx | weak to medium | strong | strong |
| Firmness of flesh | firm | firm | firm |
| Evenness of flesh color | slightly uneven | even | even |
| Distribution of flesh color | marginal and central | marginal and central | marginal and central |
| Hollow center size | medium | large | medium |
| Sweetness | medium | strong | strong |
| Texture when tasted | medium | fine | fine |
| Acidity | medium | medium | medium |
| Time of Flowering | mid-December | mid-December | early-January |
| Harvest Interval | late-January to mid-June | late-January to mid-June | early-February to mid-June |
| Type of Bearing | partially everbearing | partially everbearing | partially everbearing |

5.3 REACTION TO STRESS

TABLE 3

| | Driscoll Agoura | El Capitan | San Miguel |
|---|---|---|---|
| Reaction to Stress | | | |
| high pH | moderately resistant | moderately resistant | moderately resistant |
| high soil salt levels | moderately resistant | moderately resistant | moderately resistant |

5.4 PEST AND DISEASE RESISTANCE AND SUSCEPTIBILITY

TABLE 4

| | Driscoll Agoura | El Capitan | San Miguel |
|---|---|---|---|
| Reaction to Pests | | | |
| *Tetranychus urticae* | moderately resistant | moderately resistant | moderately resistant |
| *Lygus hesperus* | susceptible | susceptible | susceptible |

TABLE 5

| | Driscoll Agoura | El Capitan | San Miguel |
|---|---|---|---|
| Reaction to Diseases | | | |
| Botrytis fruit rot | moderately susceptible | moderately susceptible | moderately susceptible |
| Powdery mildew | moderately resistant | moderately resistant | moderately resistant |
| Verticillium wilt | susceptible | susceptible | susceptible |
| Strawberry Mottle Virus | moderately resistant | moderately resistant | moderately resistant |
| *Xanthomonas fragariae* | moderately susceptible | moderately susceptible | moderately susceptible |

5.5 ISOZYME ANALYSIS

In addition to the morphological description above, the new cultivar 'Driscoll Agoura' has been analyzed to obtain an indication of its genetic makeup to provide further means for identifying the new variety and distinguishing it from some other somewhat similar and/or related strawberry varieties. Specifically, leaf samples of 'Driscoll Agoura', 'El Capitan' and 'San Miguel' were analyzed by electrophoresis for isozyme patterns of the enzymes phosphoglucoisomeras (PGI), lecuine aminopeptidase (LAP) and phosphoglucomutase (PGM). See *J. Amer. Soc. Hort. Sci.* 106:684–687. Isozyme characterization of the three varieties is presented in Table 4, with the letters representing the banding patterns for each enzyme as designated in the above-identified article.

TABLE 6

ISOZYME ANALYSIS FOR 'DRISCOLL AGOURA', 'EL CAPITAN' AND 'SAN MIGUEL'

| Locus | Driscoll Agoura | El Capitan | San Miguel |
|---|---|---|---|
| PGI | A4 | A4 | A2 |
| LAP | B3 | B3 | B3 |
| PGM | C2 | C2 | C4 |

What is claimed is:

1. A new and distinct variety of strawberry plant, substantially as shown and described.

* * * * *